US010087237B2

(12) United States Patent
Falkenstein et al.

(10) Patent No.: US 10,087,237 B2
(45) Date of Patent: Oct. 2, 2018

(54) ISOFORM ENRICHED ANTIBODY PREPARATION AND METHOD FOR OBTAINING IT

(71) Applicant: Hoffmann-La Roche Inc., Little Falls, NJ (US)

(72) Inventors: Roberto Falkenstein, Munich (DE); Klaus Schwendner, Weilheim (DE); Bernhard Spensberger, Eberfing (DE)

(73) Assignee: F. HOFFMANN-LA ROCHE AG, Nutley, NJ (US)

( * ) Notice: Subject to any disclaimer, the term of this patent is extended or adjusted under 35 U.S.C. 154(b) by 33 days.

(21) Appl. No.: 14/934,866

(22) Filed: Nov. 6, 2015

(65) Prior Publication Data

US 2017/0066814 A1 Mar. 9, 2017

Related U.S. Application Data

(63) Continuation of application No. 13/994,673, filed as application No. PCT/EP2011/073245 on Dec. 19, 2011, now abandoned.

(30) Foreign Application Priority Data

Dec. 21, 2010 (EP) .................................... 10196287

(51) Int. Cl.
| | |
|---|---|
| *C07K 1/18* | (2006.01) |
| *C07K 16/00* | (2006.01) |
| *C07K 16/18* | (2006.01) |
| *C07K 16/30* | (2006.01) |
| *C07K 16/28* | (2006.01) |
| *C07K 16/32* | (2006.01) |

(52) U.S. Cl.
CPC ................ *C07K 16/00* (2013.01); *C07K 1/18* (2013.01); *C07K 16/18* (2013.01); *C07K 16/2863* (2013.01); *C07K 16/3015* (2013.01); *C07K 16/32* (2013.01)

(58) Field of Classification Search
None
See application file for complete search history.

(56) References Cited

U.S. PATENT DOCUMENTS

| 6,339,142 B1 * | 1/2002 | Basey ..................... C07K 1/18 |
|---|---|---|
| | | 424/133.1 |
| 2009/0105465 A1 | 4/2009 | Arunakumari et al. |
| 2010/0022757 A1 | 1/2010 | Eon-Duval et al. |
| 2012/0177640 A1 | 7/2012 | Burg et al. |

FOREIGN PATENT DOCUMENTS

| CN | 101454025 A | 6/2009 |
|---|---|---|
| EP | 1075488 | 5/2003 |
| RU | 2389552 | 5/2010 |
| WO | 2004/024866 A2 | 3/2004 |
| WO | 2004/076485 A1 | 9/2004 |
| WO | 2006/125599 | 11/2006 |
| WO | 2007/117490 A2 | 10/2007 |
| WO | 2008/025748 | 3/2008 |
| WO | 2009/058812 A1 | 5/2009 |
| WO | 2011/009623 | 1/2011 |

OTHER PUBLICATIONS

Kaltenbrunner et al., "Isoprotein analysis by ion-exchange chromatography using a linear pH gradient combined with a salt gradient" J. Chrom 639:41-49 ( 1993).

Zhou et al., "pH-conductivity hybrid gradient cation-exchange chromatography for process-scale monoclonal antibody purification" Journal of Chromatography 1175:69-80 ( 2007).

* cited by examiner

*Primary Examiner* — Daniel E Kolker
*Assistant Examiner* — James L Rogers
(74) *Attorney, Agent, or Firm* — Ginger R. Dreger

(57) ABSTRACT

Herein is reported a method for producing an antibody preparation comprising the steps of a) applying a buffered solution comprising different isoforms of an antibody to a cation exchange chromatography material, b) applying a first solution with a first conductivity to the cation exchange chromatography material, whereby the antibody isoforms remain bound to the cation exchange chromatography material, and c) applying a second solution with a second conductivity to the cation exchange chromatography material and thereby obtaining the antibody preparation, whereby the conductivity of the second solution exceeds the conductivity of the first solution by not more than 10%.

10 Claims, 6 Drawing Sheets

ISOFORM ENRICHED ANTIBODY PREPARATION AND METHOD FOR OBTAINING IT

Herein is reported a method for obtaining an antibody preparation comprising a step elution method on a strong cation exchange chromatography material.

BACKGROUND OF THE INVENTION

Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The industrial purification of pharmaceutical antibodies, especially the development, operation and validation of chromatography processes is reported by Fahrner, R. L., et al., in Biotechnol. Gen. Eng. Rev. 18 (2001) 301-327. Follman, D. K. and Fahrner, R. L. (J. Chrom. A 1024 (2004) 79-85) report a factorial screening of antibody purification processes using three chromatography steps without protein A. The capture of human monoclonal antibodies from cell culture supernatant by ion exchange media exhibiting high charge density is reported by Necina, R., et al. (Biotechnol. and Bioeng. 60 (1998) 689-698). Protein purification by ion exchange chromatography is reported in WO 99/057134. In WO 2004/076485 antibody purification by protein A and ion exchange chromatography is reported. In U.S. Pat. No. 5,429,746 antibody purification is reported. Protein purification is reported in WO 2003/066662.

WO 2006/125599 reports a method for the purification of antibodies. Antibody purification by protein A and ion exchange chromatography is reported in WO 2004/076485.

SUMMARY OF THE INVENTION

It has been found that the chromatographic separation and/or enrichment of antibody isoforms is possible with a decent conductivity increase of the mobile phase on a cation exchange chromatography material. The required conductivity increase is at most 50%, i.e. the second solution has a conductivity of from 101% to 150% of the conductivity of the first solution.

Thus, one aspect as reported herein is a method for providing an antibody preparation comprising the following steps:
 a) applying a buffered solution comprising different isoforms of an antibody to a cation exchange chromatography material,
 b) applying a first solution with a first conductivity to the cation exchange chromatography material, whereby the antibody isoforms remain bound to the cation exchange chromatography material, and
 c) applying a second solution with a second conductivity to the cation exchange chromatography material and thereby obtaining the antibody preparation,
  whereby the conductivity of the second solution exceeds the conductivity of the first solution by at least 1% but not more than 50%.

In one embodiment the conductivity of the second solution exceeds the conductivity of the first solution by at least 1% but not more than 20%.

In one embodiment the conductivity of the second solution exceeds the conductivity of the first solution by at least 1% but not more than 15%.

In one embodiment the conductivity of the second solution exceeds the conductivity of the first solution by at least 1% but not more than 10%.

In one embodiment has the solution of step a) the same conductivity as the solution of step b). In one embodiment the buffered solution comprising different isoforms of an antibody has a first conductivity and the first solution has the same (first) conductivity.

In one embodiment the cation exchange chromatography material comprises a swellable matrix. In one embodiment the swellable matrix is agarose.

In one embodiment the cation exchange chromatography material is a strong cation exchange chromatography material. In one embodiment the strong cation exchange chromatography material is a sulfopropyl-cation exchange chromatography material.

In one embodiment the first solution is changed to the second solution in a single step. In one embodiment the single step is a change from 100 vol % of the first solution to 100 vol % of the second solution.

In one embodiment the first solution is changed to the second solution in a linear gradient. In one embodiment the linear gradient is over about 30 column volumes.

In one embodiment the linear gradient is over about 20 column volumes.

In one embodiment the first solution comprises 20 mM sodium citrate.

In one embodiment the second solution comprises 20 mM sodium citrate and 5 mM sodium chloride.

In one embodiment the first solution comprises 25 mM tris (hydroxymethyl) amino methane and 10 mM sodium chloride.

In one embodiment the second solution comprises 25 mM tris (hydroxymethyl) amino methane and 70 mM sodium chloride.

In one embodiment the second solution comprises 25 mM tris (hydroxymethyl) amino methane and 45 mM sodium chloride.

In one embodiment the first and second solutions are aqueous solutions.

In one embodiment the antibody is an anti-HER2 antibody. In one embodiment the anti-HER2 antibody is the anti-HER2 antibody trastuzumab or the anti-HER2 antibody Pertuzumab. In one embodiment the anti-HER2 antibody is a humanized anti-HER2 antibody.

Herein is reported as another aspect an antibody preparation obtained by a method as reported herein. In one embodiment the antibody is an anti-HER2 antibody.

Another aspect as reported herein is a method for producing an antibody preparation comprising the following steps:
 a) cultivating a mammalian cell comprising a nucleic acid encoding the antibody and recovering the antibody from the cell or the cultivation medium,
 b) purifying the antibody by at least one column chromatographic step, wherein the at least one column chromatographic step comprises the following steps:

i) applying a buffered solution comprising different isoforms of the antibody to a cation exchange chromatography material, ii) applying a first solution with a first conductivity to the cation exchange chromatography material, whereby the antibody isoforms remain bound to the cation exchange chromatography material, and iii) applying a second solution with a second conductivity to the cation exchange chromatography material and thereby producing an antibody preparation, whereby the conductivity of the second solution exceeds the conductivity of the first solution by at least 1% but not more than 10%.

In one embodiment of all aspects as reported herein has the first solution a conductivity of from 4 mS/cm to 5 mS/cm.

DESCRIPTION OF THE INVENTION

Herein is reported a method for obtaining an antibody preparation comprising the steps of i) applying a buffered solution comprising different isoforms of an antibody to a cation exchange chromatography material, ii) applying a first solution with a first conductivity to the cation exchange chromatography material, whereby the antibody isoforms remain bound to the cation exchange chromatography material, and iii) applying a second solution with a second conductivity to the cation exchange chromatography material and thereby obtaining the antibody preparation, whereby the conductivity of the second solution exceeds the conductivity of the first solution by not more than 50%.

In general, recombinantly produced monoclonal antibodies (mAb) are recovered from the cultivation supernatant of the producing cells, such as BHK or Sp2/0 or CHO or HEK cells. Concomitantly also other proteinaceous compounds as well as different antibody isoforms are recovered. Antibody isoforms differ only in minor structural characteristics, such as glycosylation pattern, heavy chain C-terminal lysine heterogeneity, and partial deamidation of asparagine or glutamine amino acid residues.

By using general chromatographic methods an antibody is recovered from a cation exchange chromatography column/material in a single (symmetrical) peak (see e.g. Example 6 and FIG. 5).

It has now been found that antibody isoforms can be enriched or partially separated from each other by using cation exchange chromatography method. The separation/enrichment is achieved in a bind-and-elute chromatography method using a pH gradient or a salt gradient and by using a gradient with an especially slight slope.

It has been found that the enrichment of antibody isoforms in an antibody preparation is possible by column chromatography with a decent conductivity increase of the mobile phase.

In one embodiment the conductivity increase is 50% or less, i.e. the conductivity is increased from 100% to at least 101% and at most 150%, i.e. starting from a first level to a second, higher level, in order to effect elution of the antibody.

In one embodiment the conductivity increase is 10% or less, i.e. the conductivity is increased from 100% to at least 101% and at most 110%, i.e. starting from a first level to a second, higher level, in order to effect elution of the antibody.

It has been found that the matrix of the cation exchange chromatography material has to be a swellable matrix.

In one embodiment the matrix is a cross-linked saccharide. In one embodiment the saccharide is a polysaccharide. In one embodiment the polysaccharide is agarose, i.e. a polysaccharide consisting of glycosidically bound D-galactose and 3,6-anhydro-L-galactose.

The increase can be in form of a single step. Thus, the increase can be performed by a complete change of the elution solution, i.e. from 100% of the first buffered solution to 100% of the second (=elution) buffered solution.

The increase can be in form of a linear gradient. Thus, the increase can be performed by a linear change of the elution solution, i.e. from 100% of the first buffered solution to 50% to 100% of the second (=elution) buffered solution.

In one embodiment the first solution is changed to the second solution in a linear gradient. In one embodiment the linear gradient is over about 50 column volumes.

In one embodiment the linear gradient is over about 30 column volumes. In one embodiment the linear gradient is over about 20 column volumes.

General chromatographic methods and their use are known to a person skilled in the art. See for example, Heftmann, E., (ed.), Chromatography, $5^{th}$ edition, Part A: Fundamentals and Techniques, Elsevier Science Publishing Company, New York, (1992); Deyl, Z., (ed.) Advanced Chromatographic and Electromigration Methods in Biosciences, vol. 60, Elsevier Science BV, Amsterdam. The Netherlands, (1998); Poole, C. F., and Poole, S. K., Chromatography Today, Elsevier Science Publishing Company, New York, (1991); Scopes, Protein Purification: Principles and Practice, Springer Verlag, (1982); Sambrook, J., et al., (ed.), Molecular Cloning: A Laboratory Manual, Second Edition, Cold Spring Harbor Laboratory Press, Cold Spring Harbor, N.Y., (1989); or Ausubel, F. M., et al., (eds.), Current Protocols in Molecular Biology, John Wiley & Sons, Inc., New York, (1998).

In the following Table the conductivities of some generally used buffer solutions is given as a reference.

TABLE

| buffer | NaCl [g/l] | buffer salt [g/l] | pH | cond. [mS/cm] | conductivity change [%] |
|---|---|---|---|---|---|
| 10 mM sodium citrate | — | 1.92 | 5.5 | 1.74 | — |
| 20 mM sodium citrate | — | 3.84 | 5.5 | 3.49 | +101 |
| 30 mM sodium citrate | — | 5.76 | 5.5 | 5.05 | +190 |
| 40 mM sodium citrate | — | 7.68 | 5.5 | 6.45 | +271 |
| 50 mM sodium citrate | — | 9.60 | 5.5 | 8.04 | +362 |
| 10 mM sodium citrate with 25 mM NaCl | 1.46 | 1.92 | 5.5 | 4.87 | — |
| 10 mM sodium citrate with 50 mM NaCl | 2.92 | 1.92 | 5.5 | 7.34 | +51 |
| 10 mM sodium citrate with 100 mM NaCl | 5.84 | 1.92 | 5.5 | 12.21 | +151 |
| 10 mM sodium citrate with 150 mM NaCl | 8.77 | 1.92 | 5.5 | 17.17 | +253 |

TABLE-continued

| buffer | NaCl [g/l] | buffer salt [g/l] | pH | cond. [mS/cm] | conductivity change [%] |
|---|---|---|---|---|---|
| 10 mM sodium citrate with 200 mM NaCl | 11.69 | 1.92 | 5.5 | 21.70 | +346 |
| 20 mM sodium citrate with 25 mM NaCl | 1.46 | 3.84 | 5.5 | 6.65 | — |
| 20 mM sodium citrate with 50 mM NaCl | 2.92 | 3.84 | 5.5 | 9.12 | +37 |
| 20 mM sodium citrate with 100 mM NaCl | 5.84 | 3.84 | 5.5 | 13.82 | +108 |
| 20 mM sodium citrate with 150 mM NaCl | 8.77 | 3.84 | 5.5 | 18.37 | +176 |
| 20 mM sodium citrate with 200 mM NaCl | 11.69 | 3.84 | 5.5 | 22.80 | +243 |
| 30 mM sodium citrate with 25 mM NaCl | 1.46 | 5.76 | 5.5 | 8.37 | — |
| 30 mM sodium citrate with 50 mM NaCl | 2.92 | 5.76 | 5.5 | 10.65 | +27 |
| 30 mM sodium citrate with 100 mM NaCl | 5.84 | 5.76 | 5.5 | 15.15 | +81 |
| 30 mM sodium citrate with 150 mM NaCl | 8.77 | 5.76 | 5.5 | 19.69 | +135 |
| 30 mM sodium citrate with 200 mM NaCl | 11.69 | 5.76 | 5.5 | 24.10 | +188 |
| 40 mM sodium citrate with 25 mM NaCl | 1.46 | 7.68 | 5.5 | 9.78 | — |
| 40 mM sodium citrate with 50 mM NaCl | 2.92 | 7.68 | 5.5 | 12.12 | +24 |
| 40 mM sodium citrate with 100 mM NaCl | 5.84 | 7.68 | 5.5 | 16.71 | +71 |
| 40 mM sodium citrate with 150 mM NaCl | 8.77 | 7.68 | 5.5 | 21.20 | +117 |
| 40 mM sodium citrate with 200 mM NaCl | 11.69 | 7.68 | 5.5 | 25.30 | +159 |
| 50 mM sodium citrate with 25 mM NaCl | 1.46 | 9.60 | 5.5 | 11.31 | — |
| 50 mM sodium citrate with 50 mM NaCl | 2.92 | 9.60 | 5.5 | 13.61 | +20 |
| 50 mM sodium citrate with 100 mM NaCl | 5.84 | 9.60 | 5.5 | 18.19 | +61 |
| 50 mM sodium citrate with 150 mM NaCl | 8.77 | 9.60 | 5.5 | 22.40 | +98 |
| 50 mM sodium citrate with 200 mM NaCl | 11.69 | 9.60 | 5.5 | 26.70 | +136 |
| 25 mM MES with 50 mM NaCl | 2.92 | 5.53 | 5.6 | 7.65 | — |
| 25 mM MES with 95 mM NaCl | 5.55 | 5.53 | 5.6 | 12.15 | +59 |
| 25 mM MES with 50 mM NaCl and 5 g/l Herceptin ® | — | 7.48 | 5.53 | 7.66 | — |
| 25 mM MES with 95 mM NaCl and 5 g/l Herceptin ® | — | 11.26 | 5.50 | 12.22 | +60 |
| 25 mM MES with 50 mM NaCl and 15 g/l Herceptin ® | — | 7.11 | 5.50 | 7.52 | — |
| 25 mM MES with 95 mM NaCl and 15 g/l Herceptin ® | — | 9.22 | 5.50 | 11.97 | +59 |
| 20 mM sodium citrate | — | 3.84 | 6.2 | 4.22 | — |
| 20 mM sodium citrate with 5 mM NaCl | 0.29 | 3.84 | 6.2 | 4.62 | +9 |

The term "applying to" denotes a partial step of a purification method in which a solution is brought in contact with a chromatography material. This denotes that either a) the solution is added to a chromatographic device in which the chromatography material is contained, or b) that the chromatography material is added to the solution. In case a) the solution passes through the device allowing for an interaction between the chromatography material and the substances contained in solution. Depending on the conditions, such as e.g. pH, conductivity, salt concentration, temperature, and/or flow rate, some substances of the solution can be bound to the chromatography material and other substances can be recovered from the chromatography material. The substances remaining in solution or recovered from the chromatography material can be found in the flow-through. The "flow-through" denotes the solution obtained after the passage of the device, which may either be the applied solution or a buffered solution, which is used to wash the column or to cause elution of substances bound to the chromatography material. In one embodiment the device is a column or a cassette. In case b) the chromatography material can be added, e.g. as a solid, to the solution, e.g. containing the substance of interest to be purified, allowing for an interaction between the chromatography material and the substances in solution. After the interaction the chromatography material is removed, e.g. by filtration, and the substance bound to the chromatography material are also removed therewith from the solution whereas the substances not bound to the chromatography material remain in solution.

The term "bind-and-elute mode" denotes an operation mode of a chromatography step, in which a solution containing a substance of interest to be purified is applied to a chromatography material, whereby the substance of interest binds to the chromatography material. Thus, the substance of interest is retained on the chromatography material whereas substances not of interest are removed with the flow-through or the supernatant. The substance of interest is afterwards recovered from the chromatography material in a second step with an elution solution. In one embodiment the method as reported herein is operated in bind-and-elute mode.

The solutions employed in the method as reported herein are crude or buffered solutions. The term "buffered solution" denotes a solution in which changes of pH due to the addition or release of acidic or alkaline substances is leveled by the dissolved buffer substance. Any buffer substance with such properties can be used. Generally pharmaceutically acceptable buffers substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In another embodiment the buffer solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate.

The terms "gradient elution" and "gradient elution method", which are used interchangeably within this application, denote a method wherein the conductivity of a solution causing elution, i.e. the recovery of a bound compound from a chromatography material, is changed, i.e. raised or lowered, continuously, i.e. the concentration is changed by a sequence of small steps each not bigger than a change of 2%, or of 1% of the concentration of the substance causing elution. In this "continuous elution" one or more conditions, for example the pH, the ionic strength, concentration of a salt, and/or the flow of a chromatography, may be changed linearly or exponentially or asymptotically. In one embodiment the change is linear.

The term "step elution" denotes a method wherein e.g. the concentration of a substance causing elution, i.e. the recovery of a bound substance from a chromatography material, is raised or lowered at once, i.e. directly from one value/level to the next value/level. In this "step elution" one or more conditions, for example the pH, the ionic strength, concentration of a salt, and/or the flow of a chromatography, can be changed all at once from a first, e.g. starting, value to a second, e.g. final, value. Thus, the conditions are changed incrementally, i.e. stepwise, in contrast to a linear change.

The term "ion exchange chromatography material" denotes an immobile high molecular weight matrix that carries covalently bound charged substituents used as stationary phase in ion exchange chromatography. For overall charge neutrality not covalently bound counter ions are bound thereto. The "ion exchange chromatography material" has the ability to exchange its not covalently bound counter ions for similarly charged ions of the surrounding solution. Depending on the charge of its exchangeable counter ions the "ion exchange resin" is referred to as cation exchange resin or as anion exchange resin. Depending on the nature of the charged group (substituent) the "ion exchange resin" is referred to as, e.g. in the case of cation exchange resins, sulfonic acid resin (S), or sulfopropyl resin (SP), or carboxymethyl resin (CM).

Different types of ion exchange materials, i.e. stationary phases, are available under different names and from a multitude of companies such as e.g. cation exchange materials Bio-Rex® (e.g. type 70), Chelex® (e.g. type 100), Macro-Prep® (e.g. type CM, High S, 25 S), AGO (e.g. type 50W, MP) all available from BioRad Laboratories, WCX 2 available from Ciphergen, Dowex® MAC-3 available from Dow chemical company, Mustang C and Mustang S available from Pall Corporation, Cellulose CM (e.g. type 23, 52), hyper-D, partisphere available from Whatman plc., Amberlite® IRC (e.g. type 76, 747, 748), Amberlite® GT 73, Toyopearl® (e.g. type SP, CM, 650M) all available from Tosoh Bioscience GmbH, CM 1500 and CM 3000 available from BioChrom Labs, SP-Sepharose™, CM-Sepharose™ available from GE Healthcare, Poros resins available from PerSeptive Biosystems, Asahipak ES (e.g. type 502C), CXpak P, IEC CM (e.g. type 825, 2825, 5025, LG), IEC SP (e.g. type 420N, 825), IEC QA (e.g. type LG, 825) available from Shoko America Inc., 50W cation exchange resin available from Eichrom Technologies Inc. In one embodiment the cation exchange material is a strong cation exchange material such as Macro-Prep® High S or 25S, or MacroCap SP, or Toyopearl® SP 650M, or Source S, or SP Sepharose, or POLYCAT A, or Mono S, or Highscreen SP.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

The term "under conditions suitable for binding" and grammatical equivalents thereof as used within this application denotes that a substance of interest, e.g. antibody isoforms, binds to a stationary phase when brought in contact with it, e.g. an ion exchange material. This does not necessarily denote that 100% of the substance of interest is bound but essentially 100% of the substance of interest is bound, i.e. at least 50% of the substance of interest is bound, preferably at least 75% of the substance of interest is bound, preferably at least 85% of the substance of interest is bound, more preferably more than 95% of the substance of interest is bound to the stationary phase.

The term "therapeutic antibody" denotes an antibody which is tested in clinical studies for approval as human therapeutic and which can be administered to an individual for the treatment of a disease. In one embodiment the antibody is a therapeutic antibody. In another embodiment the therapeutic antibody is a monoclonal antibody. In a further embodiment the therapeutic antibody is obtained from a great ape or an animal transformed with a human antibody locus or a human monoclonal antibody or a humanized monoclonal antibody. In one embodiment the therapeutic antibody is a human monoclonal antibody. In a further embodiment the therapeutic antibody is a humanized monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, in one embodiment antibodies against ALK, adhesion related kinase receptor (e.g., Axl), or ERBB receptors (e.g., EGFR, ERBB2, ERBB3, ERBB4), or erythropoietin-producing hepatocellular (EPH) receptors (e.g., EphA1; EphA2, EphA3, EphA4, EphA5, EphA6, EphA7, EphA8, EphB1, EphB2, EphB3, EphB4, EphB5, EphB6), or fibroblast growth factor (FGF) receptors (e.g., FGFR1, FGFR2, FGFR3, FGFR4, FGFR5), or Fgr, or IGF1R, or Insulin Receptor, or LTK, or M-CSFR, or MUSK, or platelet-derived growth factor (PDGF) receptors (e.g., PDGFR-A, PDGFR-B), or RET, or ROR1, or ROR2, or ROS, or RYK, or vascular endothelial growth factor (VEGF) receptors (e.g., VEGFR1/FLT1, VEGFR2/FLK1, VEGF3), or tyrosine kinase with immunoglobulin-like and EGF-like domains (TIE) receptors (e.g., TIE-1, TIE-2/TEK), or Tec, or TYRO10, or insulin-like growth factor (IGF) receptors (e.g., INS-R, IGF-IR, IR-R), or Discoidin Domain (DD) receptors (e.g., DDR1, DDR2), or receptor for c-Met (MET), or recepteur d'origine nantais (RON, also known as macrophage stimulating 1 receptor), or Flt3 (fms-related tyrosine kinase 3), or colony stimulating factor 1 (CSF1) receptor, or receptor for c-kit (KIT, or SCFR), or insulin receptor related (IRR) receptors, or CD19, or CD20, or HLA-DR, or CD33, or CD52, or G250, or GD3, or PSMA, or CD56, or CEA, or Lewis Y antigen, or IL-6 receptor.

The term "antibody" encompasses the various forms of antibody structures including whole antibodies and antibody fragments. The antibody as reported herein is in one embodiment a human antibody, a humanized antibody, a chimeric antibody, or a T cell antigen depleted antibody. Genetic engineering of antibodies is e.g. described in Morrison, S. L., et al., Proc. Natl. Acad. Sci. USA 81 (1984) 6851-6855; U.S. Pat. No. 5,202,238 and U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125. Depending on the amino acid sequence of the constant region of the heavy chains, antibodies are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called α (IgA), δ (IgD), ε (IgE), γ (IgG), and μ (IgM), respectively. The term "antibody of human IgG1 class" denotes an antibody in which the amino acid sequence of the constant domains is derived from the amino acid sequence of human IgG1. The term includes human antibodies, humanized antibodies, chimeric antibodies and antibody conjugates.

"Humanized" forms of non-human (e.g. rodent) antibodies are chimeric antibodies that contain partial sequences derived from a non-human antibody and from a human antibody. For the most part, humanized antibodies are derived from a human antibody (recipient antibody), in which residues from a hypervariable region are replaced by residues from a hypervariable region of a non-human species (donor antibody), such as mouse, rat, rabbit, or non-human primate, having the desired specificity and affinity. In some instances, framework region (FR) residues of the human antibody are replaced by corresponding non-human residues. Furthermore, humanized antibodies may comprise further modifications, e.g. amino acid residues that are not found in the recipient antibody or in the donor antibody. Such modifications result in variants of such recipient or donor antibody, which are homologous but not identical to the corresponding parent sequence. These modifications are made to further refine antibody performance.

In general, the humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally will also comprise at least a portion of an antibody constant region, typically that of a human antibody.

Methods for humanizing non-human antibodies have been described in the art. In one embodiment a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some hypervariable region residues and possibly some framework region residues are substituted by residues from analogous sites in rodent or non-human primate antibodies.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "chimeric antibody" denotes an antibody comprising a variable domain, i.e. binding region, from a first species and at least a portion of a constant region derived from a different second source or species, usually prepared by recombinant DNA techniques.

Amino acid sequence variants of antibodies can be prepared by introducing appropriate modifications into the nucleotide sequence encoding the antibody chains, or by peptide synthesis. Such modifications include, for example, deletions from, and/or insertions into and/or substitutions of residues within the amino acid sequences of the interferon. Any combination of deletion, insertion, and substitution can be made to arrive at the final construct, provided that the final construct possesses the antigen binding properties as the parent antibody.

Conservative amino acid substitutions are shown in Table 1 under the heading of "preferred substitutions". More substantial changes are provided in the following Table under the heading of "exemplary substitutions", and as described below in reference to amino acid side chain classes. Amino acid substitutions may be introduced into the antibody chains and the products screened for retention of the biological activity of the parent antibody.

TABLE

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Hudziak, R. M., et al., Mol. Cell. Biol. 9 (1989) 1165-1172 describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α (see also U.S. Pat. No. 5,677,171). The HER2 antibodies discussed in Hudziak, R. M., et al. are further characterized in Fendly, B. M., et al., Cancer Research 50 (1990) 1550-1558; Kotts, C. E., et al., In Vitro 26 (1990) 59A; Sarup, J. C., et al., Growth Regulation 1 (1991) 72-82; Shepard, H. M., et al., J. Clin. Immunol. 11 (1991) 117-127; Kumar, R., et al., Mol. Cell. Biol. 11 (1991) 979-986; Lewis, G. D., et al., Cancer Immunol. Immunother. 37 (1993) 255-263; Pietras, R. J., et al., Oncogene 9 (1994) 1829-1838; Vitetta, E. S., et al., Cancer Research 54 (1994) 5301-5309; Sliwkowski, M. X., et al., J. Biol. Chem. 269 (1994) 14661-14665; Scott, G. K., et al., J. Biol. Chem. 266 (1991) 14300-14305; D'souza, B., et al., Proc. Natl. Acad. Sci. 91 (1994) 7202-7206; Lewis, G. D., et al., Cancer Research 56 (1996) 1457-1465; and Schaefer, G., et al., Oncogene 15 (1997) 1385-1394.

A recombinant humanized version of the murine HER2 antibody 4D5 (huMAb4D5-8, rhuMab HER2, trastuzumab or HERCEPTIN®; see U.S. Pat. No. 5,821,337) is clinically active in patients with HER2 overexpressing metastatic breast cancers that have received extensive prior anti-cancer therapy (Baselga, J., et al., J. Clin. Oncol. 14 (1996) 737-744). Trastuzumab received marketing approval from the Food and Drug Administration Sep. 25, 1998 for the treatment of patients with metastatic breast cancer whose tumors overexpress the HER2 protein.

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO 93/21319) and humanized 2C4 antibodies as described in WO 01/000245 expressly incorporated herein by reference.

Other HER2 antibodies with various properties have been described in Tagliabue, E., et al., Int. J. Cancer 47 (1991) 933-937; McKenzie, S. J., et al., Oncogene 4 (1989) 543-548; Maier, L. A., et al., Cancer Res. 51 (1991) 5361-5369; Bacus, S. S., et al., Molecular Carcinogenesis 3 (1990) 350-362; Stancovski, I., et al., PNAS USA 88 (1991) 8691-8695; Bacus, S. S., et al., Cancer Research 52 (1992) 2580-2589; Xu, F., et al., Int. J. Cancer 53 (1993) 401-408; WO 94/00136; Kasprzyk, P. G., et al., Cancer Research 52 (1992) 2771-2776; Hancock, M. C., et al., Cancer Res. 51 (1991) 4575-4580; Shawver, L. K., et al., Cancer Res. 54 (1994) 1367-1373; Arteaga, C. L., et al., Cancer Res. 54 (1994) 3758-3765; Harwerth, I. M., et al., J. Biol. Chem. 267 (1992) 15160-15167; U.S. Pat. No. 5,783,186; and Klapper, L. N., et al., Oncogene 14 (1997) 2099-2109.

Pertuzumab (see e.g. WO 01/000245) is the first of a new class of agents known as HER dimerization inhibitors (HDIs). Pertuzumab binds to HER2 at its dimerization domain, thereby inhibiting its ability to form active dimer receptor complexes and thus blocking the downstream signal cascade that ultimately results in cell growth and division (see Franklin, M. C., Cancer Cell 5 (2004) 317-328). Pertuzumab is a fully humanized recombinant monoclonal antibody directed against the extracellular domain of HER2. Binding of Pertuzumab to the HER2 on human epithelial cells prevents HER2 from forming complexes with other members of the HER family (including EGFR, HER3, HER4) and probably also HER2 homodimerization. By blocking complex formation, Pertuzumab prevents the growth stimulatory effects and cell survival signals activated by ligands of HER1, HER3 and HER4 (e.g. EGF, TGFα, amphiregulin, and the heregulins). Another name for Pertuzumab is 2C4. Pertuzumab is a fully humanized recombinant monoclonal antibody based on the human IgG1(K) framework sequences. The structure of Pertuzumab consists of two heavy chains (449 residues) and two light chains (214 residues). Compared to Trastuzumab (Herceptin®), Pertuzumab has 12 amino acid differences in the light chain and 29 amino acid differences in the IgG1 heavy chain.

The term "hydrophobic" denotes compounds which are predominantly characterized by van der Waals interactions as major or even solely intermolecular interactions to be considered. The term "predominantly" in this context indicates that in principle, hydrophilic compounds may be also possible and present but only have a minor importance for the general characterization of the chemical and/or physical properties of the respective analyte. The opposite to the term "hydrophobic" in context of the present invention is the term "hydrophilic" which denotes those compounds characterized by hydrogen bonding and which have a strong polar and/or protic character. In one embodiment the ion exchange chromatography material matrix is a hydrophobic matrix.

The term "protic" denotes the property of containing or releasing proton(s) and/or of forming hydrogen bond(s), such as, for example water, alcohols, amines etc. The release of protons from a molecule is also known to the skilled person as dissociation. The simplest protic solvent is water, which in a simplified way dissociates into a proton and a hydroxyl ion. Well-known protic solvents are, for example, alcohols in which the release of the proton generally occurs at the hydroxyl group leaving a negatively charged oxygen atom of the former hydroxyl group because the electronegative oxygen atom is able to stabilize the resulting negative charge. Even carbonic acids may be considered as protic solvents, provided that the release of protons from the carboxylic function does not lead to a chemical reaction with a particular substance which for example is to be dissolved in the particular solution. A further group of protic solvents is represented by amines which contain "protons", strictly speaking hydrogen atoms, in their amino group as well as a free electron pair at the corresponding nitrogen atom for forming a hydrogen bond.

The term "mobile phase" denotes any mixtures of water and/or aqueous buffers, and organic solvents being suitable to elute analytes from a chromatography column. The term "to elute" or "eluting", respectively, in the present context is used as known to the expert skilled in the art and denotes the dissolution, optionally the displacement, of adsorbed substance(s) from solids or adsorbents, which are impregnated with fluids, i.e., the column material to which the substance(s) is/are adsorbed.

The term "adsorption" denotes the accumulation of substances from a fluid, e.g. a mobile phase, at the boundary phase formed of the fluid with a substance, wherein the latter is able to adsorb the substances at its surface. This adsorption leads to an accumulation of the adsorbed substances at the particular surface. The substance that is able to accumulate substances at its surface is often referred to as adsorbent and the adsorbed material as adsorbate. The term adsorption is usually distinguished from the term "absorption" which beyond the accumulation at a surface also refers to the penetration of the accumulated substances into the interior of the adsorbing solid or fluid. In general, adsorption is a physical process in which substances usually molecules adhere to a surface of the adsorbent and thus, are accumulated at the respective surface. The forces being responsible for this adherence are considered to be physical forces rather than chemical bonds and thus, adsorption is also known in the art as physical adsorption or physisorption, which does not necessarily exclude chemical bonding of substances to the surface. The physical forces involved in the adsorption of substances to a surface are in most cases van der Waals-forces, London forces or dipole/dipole interactions, for example hydrogen bonds, or dipole-induced dipole interactions, wherein these terms are used as either explained above or as normally used in context with adsorption.

In (column) chromatography usually solvents are used as eluent, i.e., eluting agent in which the substance(s) which are to be eluted are at least sufficiently soluble.

The term "swellable matrix" denotes any swellable polymer gel on the basis of monomers which are chemically or physically connected with one another under formation of a three-dimensional network. The chemical connectivity is realized through bond formation, whereas the physical construction of swellable matrices may be on the basis of electrostatic, hydrophobic or dipole/dipole interactions between single areas of the respective polymer segments. The term "swellable matrix" denotes in one embodiment polymer gels in which the three-dimensional network is obtained through chemical bond formation. The network itself can consist of one or more different components. In the presence of a suitable solvent the network swells under simultaneous incorporation of the respective solvent into its three-dimensional network until an equilibrium volume of incorporated volume is reached. In another terminology the swollen state of the network is known as gel and the non-swollen state is known as gelator. In context of the present invention the term swellable matrix also encompasses the meaning of the term gelator.

The term "swellable matrix" denotes only those gels constructed of hydrophilic but water-insoluble polymers which swell in the presence of water as solvent. The affinity of swellable matrices to water is attributed to salvation and entropic effects of the polymeric network. Beside water also pure hydrophilic organic solvents, such as, for example methanol, ethanol and dimethyl formamide as well as their respective aqueous solutions containing the organic solvent in variable amounts effect swelling of the swellable matrices, wherein the term hydrophilic is understood as explained above. Accordingly, the term swellable matrix is no longer limited to only those gels that swell under incorporation of water into their network but also under incorporation of hydrophilic organic solvents and/or of their respective aqueous solutions and/or mixtures of variable composition.

In context with swellable matrices, cross-linking is of major importance because it leads to the formation of the three-dimensional structure and also to the formation of cavities, which allows the swelling behavior of the matrix. Moreover, the degree of cross-linking necessarily affects the size of the pores of the obtained swellable matrices.

Thus, one aspect as reported herein is a method for enriching antibody isoforms in an antibody preparation comprising the following steps:

a) applying a buffered solution comprising different isoforms of an antibody to a cation exchange chromatography material, b) applying a first solution with a first conductivity to the cation exchange chromatography material, whereby the antibody isoforms remain bound to the cation exchange chromatography material, and c) applying a second solution with a second conductivity to the cation exchange chromatography material and thereby obtaining the antibody preparation with enriched antibody isoforms, whereby the conductivity of the second solution exceeds the conductivity of the first solution by not more than 50%.

One embodiment is a method for enriching antibody isoforms in an antibody preparation comprising the following steps:

a) applying a buffered solution comprising different isoforms of an antibody to a cation exchange chromatography material, b) applying a first solution with a first conductivity to the cation exchange chromatography material, whereby the antibody isoforms remain bound to the cation exchange chromatography material, and c) applying a second solution with a second conductivity to the cation exchange chromatography material and thereby obtaining the antibody preparation with enriched antibody isoforms, whereby the conductivity of the second solution exceeds the conductivity of the first solution by not more than 10%.

The solution of step a) has in one embodiment the same conductivity as the solution of step b).

An "antibody isoform" denotes a version of an antibody with small differences with respect to another isoform of the same antibody. The "same antibody" is an antibody with the same amino acid sequence except for the modification(s) of the specific isoform. Different forms of an antibody can result during transcription or translation of the sequence encoding the antibody, as well as differences arising from the processing and secretion of the antibody from a cell, from purification, from formulation and from degradation during storage. An antibody isoform can vary in amino acid sequence, multimerization, glycosylation and other post translational modifications. A "glycoform" is an isoform where different versions of a glycoprotein have different polysaccharides attached to them, by posttranslational modifications. Also antibody heavy chain C-terminal processing of lysine residues can be a source of antibody structural variation.

It has been found that antibody isoforms in an antibody preparation can be enriched or even partially separated using a cation exchange column chromatography method. This can be achieved in a bind-and-elute method using a pH or salt gradient, either linear or step, for recovering of the antibody from the chromatography material. The method is especially effective by using a gradient with a slight slope, i.e. having a relative change of the pH value or increase of the conductivity of 50% or less of the starting value, especially of 10% or less of the starting value. As the different antibody isoforms are visible as at least semi-detached peaks in the corresponding chromatogram the isoform composition of an antibody preparation can be adjusted based on the selected and combined elution fractions spanning the respective peaks in the chromatogram.

In more detail it has been found that the enrichment of antibody isoforms in an antibody preparation can be achieved with a decent increase of the conductivity of the mobile phase applied to a cation exchange chromatography material.

The term "antibody preparation" denotes a mixture comprising different isoforms of the same antibody.

In FIG. 1 an elution chromatogram of a column chromatographic separation using a linear gradient from 20 vol % elution buffer to 60 vol % elution buffer is shown (wash buffer comprises 20 mM sodium citrate, elution buffer comprises 20 mM sodium citrate and 100 mM sodium chloride). It can be seen that the antibody isoforms are recovered in a single peak. A slight pre-peak can be seen.

In FIG. 2 an elution chromatogram of a column chromatographic separation using a step gradient of 24 vol % elution buffer is shown (wash buffer comprises 20 mM sodium citrate, elution buffer comprises 20 mM sodium citrate and 100 mM sodium chloride). It can be seen that the antibody isoforms are recovered in a semi-detached peak.

In FIG. 3 an elution chromatogram of a column chromatographic separation using a step gradient of 15 vol % elution buffer is shown (wash buffer comprises 20 mM sodium citrate, elution buffer comprises 20 mM sodium citrate and 80 mM sodium chloride). It can be seen that the antibody isoforms are recovered in two semi-detached peak, wherein the first peak shows a pre-peak.

In FIG. 4 an elution chromatogram of a column chromatographic separation using a step gradient of 100 vol % elution buffer is shown (wash buffer comprises 20 mM sodium citrate, elution buffer comprises 20 mM sodium citrate and 5 mM sodium chloride). It can be seen that the antibody isoforms are recovered in three semi-detached peaks.

In FIG. 5 an elution chromatogram of a column chromatographic separation using a single step elution method wherein the conductivity was increased from 100% to 159%. It can be seen that the antibody is recovered as a single peak.

In FIG. 6 an elution chromatogram of a column chromatographic separation using a linear gradient of from 100 vol % of the first buffer solution to 60 vol % of the second buffer solution is shown (first buffer comprises 25 mM TRIS and 10 mM sodium chloride; second buffer comprises 25 mM TRIS and 70 mM sodium chloride; both buffer have a pH value of pH 7.4). It can be seen that the antibody isoforms are recovered in three peaks.

In one embodiment the conductivity increase is 50% or less, i.e. the conductivity is increased to 150% or less. Thus, the second solution has a conductivity that is 101% to 150% of the conductivity of the first solution. The increase can be in form of a single step or a linear gradient. The increase can be performed by a complete change of the elution solution, i.e. from 100% of the first (=wash) solution to 100% of the second (=elution) solution.

In one embodiment the conductivity increase is 10% or less, i.e. the conductivity is increased to 110% or less. Thus, the second solution has a conductivity that is 101% to 110% of the conductivity of the first solution. The increase can be in form of a single step or a linear gradient. The increase can be performed by a complete change of the elution solution, i.e. from 100% of the first (=wash) solution to 100% of the second (=elution) solution.

In one embodiment the linear gradient comprises three linear gradients each with different slope.

In one embodiment the first linear gradient is for 18 to 20 column volumes, the second linear gradient is for 2 to 4 column volumes, and the third linear gradient is for 6 to 8 column volumes. In one embodiment the first linear gradient is to about 115% of the conductivity of the first solution, the second linear gradient is to about 137% of the conductivity of the first solution, and the third linear gradient is to about 150% of the conductivity of the first solution.

It has also been found that the matrix of the cation exchange chromatography material has to be a swellable matrix. In one embodiment the matrix is a cross-linked saccharide. In a further embodiment the saccharide is a polysaccharide. In another embodiment the polysaccharide is agarose, i.e. a polysaccharide consisting of glycosidically bound D-galactose and 3,6-anhydro-L-galactose.

Thus, another aspect as reported herein is a method for producing an antibody preparation comprising the following steps:
  a) cultivating a mammalian cell comprising a nucleic acid encoding the antibody and recovering the antibody from the cell or the cultivation medium,
  b) purifying the antibody by at least one column chromatographic step, wherein the at least one chromatographic step comprises the following steps:
    i) applying a buffered solution comprising different isoforms of the antibody to a cation exchange chromatography material,
    ii) applying a first solution with a first conductivity to the cation exchange chromatography material, whereby the antibody isoforms remain bound to the cation exchange chromatography material, and
    iii) applying a second solution with a second conductivity to the cation exchange chromatography material and thereby producing the antibody preparation, whereby the conductivity of the second solution exceeds the conductivity of the first solution by not more than 10%.

In one embodiment the method is a method for producing in large scale. In another embodiment large scale is of 1 g or more antibody preparation.

The following examples and figures are provided to aid the understanding of the present invention, the true scope of which is set forth in the appended claims. It is understood that modifications can be made in the procedures set forth without departing from the spirit of the invention.

EXAMPLES

Materials & Methods

An exemplary immunoglobulin which can be used in the method as reported herein is an anti-HER2 antibody reported in WO 92/022653, WO 99/057134, WO 97/04801, U.S. Pat. No. 5,677,171 and U.S. Pat. No. 5,821,337 (incorporated herein by reference).

Analytical Size Exclusion Chromatography:
   resin: TSK 3000 (Tosohaas)
   column: 300×7.8 mm
   flow rate: 0.5 ml/min
   buffered solution: 200 mM potassium phosphate containing
     250 mM potassium chloride, adjusted to pH 7.0
   wavelength: 220 nm Analytical IE-HPLC
   resin: Dionex ProPac™ WCX-10 Analytical Grade
   column: 4×250 mm
   flow rate: 0.8 ml/min
   buffer A: 10 mM sodium phosphate, adjusted to pH 7.5
   buffer B: 10 mM sodium phosphate, adjusted to pH 7.5 and supplemented with 0.1 M sodium chloride
   starting conditions: 85 vol % buffer A and 15 vol % buffer B
   gradient: to 55 vol % buffer B in 9 column volumes
   detection wavelength: 214 nm
   sample amount: 50 μg Sample and carboxypeptidase B are diluted to a final concentration of 1 mg/ml with sample buffer. To the diluted sample solution 1% (w/w) of the diluted carboxypeptidase solution is added.

Example 1

Figure 1:
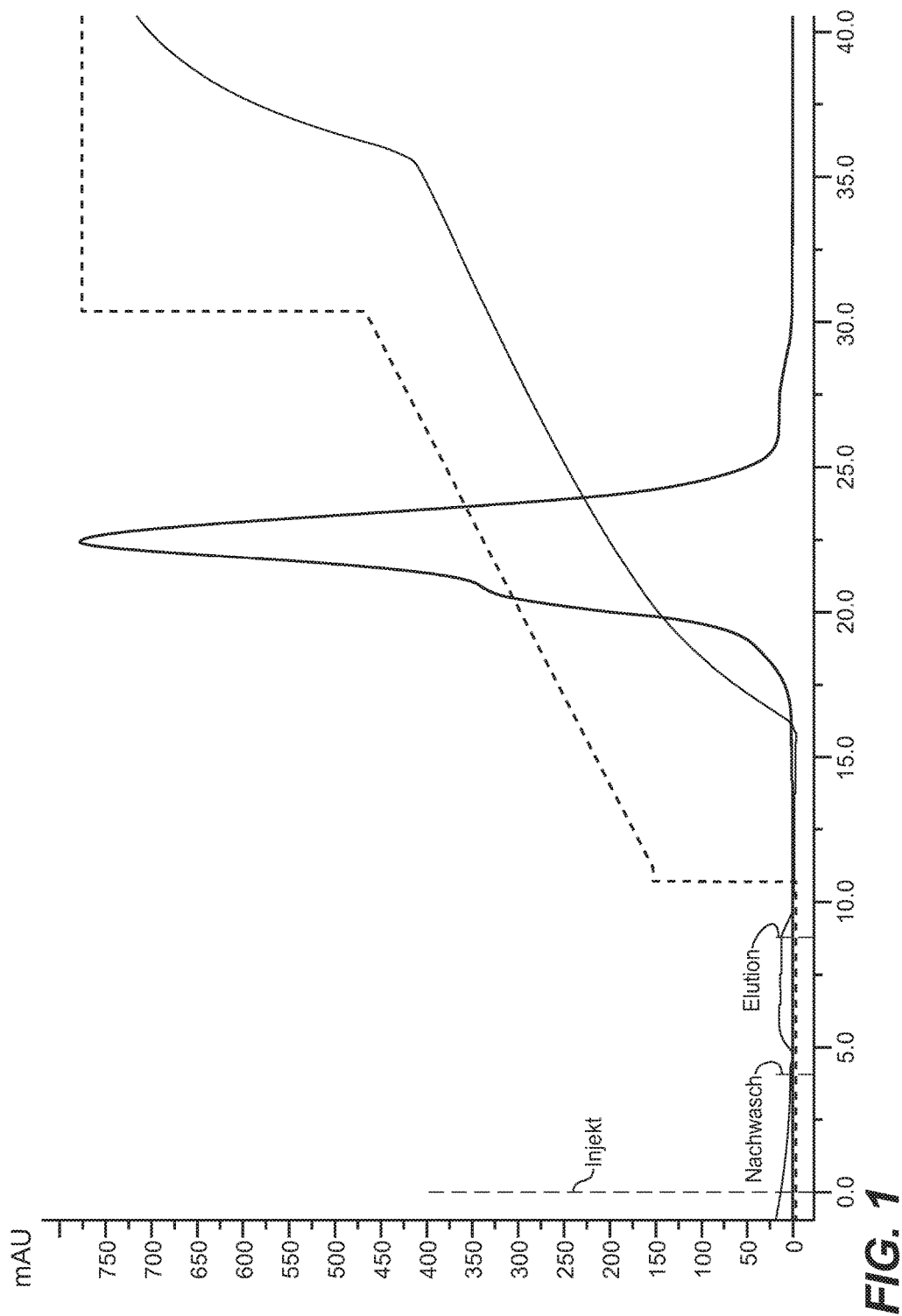
FIG. 1 Elution chromatogram of a column chromatographic separation using a linear gradient from 20 vol % elution buffer to 60 vol % elution buffer is shown (wash buffer comprises 20 mM sodium citrate, elution buffer comprises 20 mM sodium citrate and 100 mM sodium chloride).

Chromatography with Combination Gradient Elution to 60 Vol % Elution Buffer on SP-Sepharose Chromatographic Conditions:
Resin: Highscreen SP-Sepharose
Flow rate: 1.2 ml/min
Equilibration: 20 mM sodium citrate, adjusted to pH 6.2
Loading: 1 g protein/1 chromatography material
Wash: 20 mM sodium citrate, adjusted to pH 6.2
Elution: 20 mM sodium citrate, adjusted to pH 6.2 and supplemented with 100 mM sodium chloride
Elution Method:
   combination of step and linear gradient
   step to 20% elution buffer and afterwards linear gradient to 60% elution buffer The elution chromatogram is shown in FIG. 1. It can be seen that the antibody isoforms can be recovered in a single peak. A slight pre-peak can be seen.

Example 2

Figure 2:
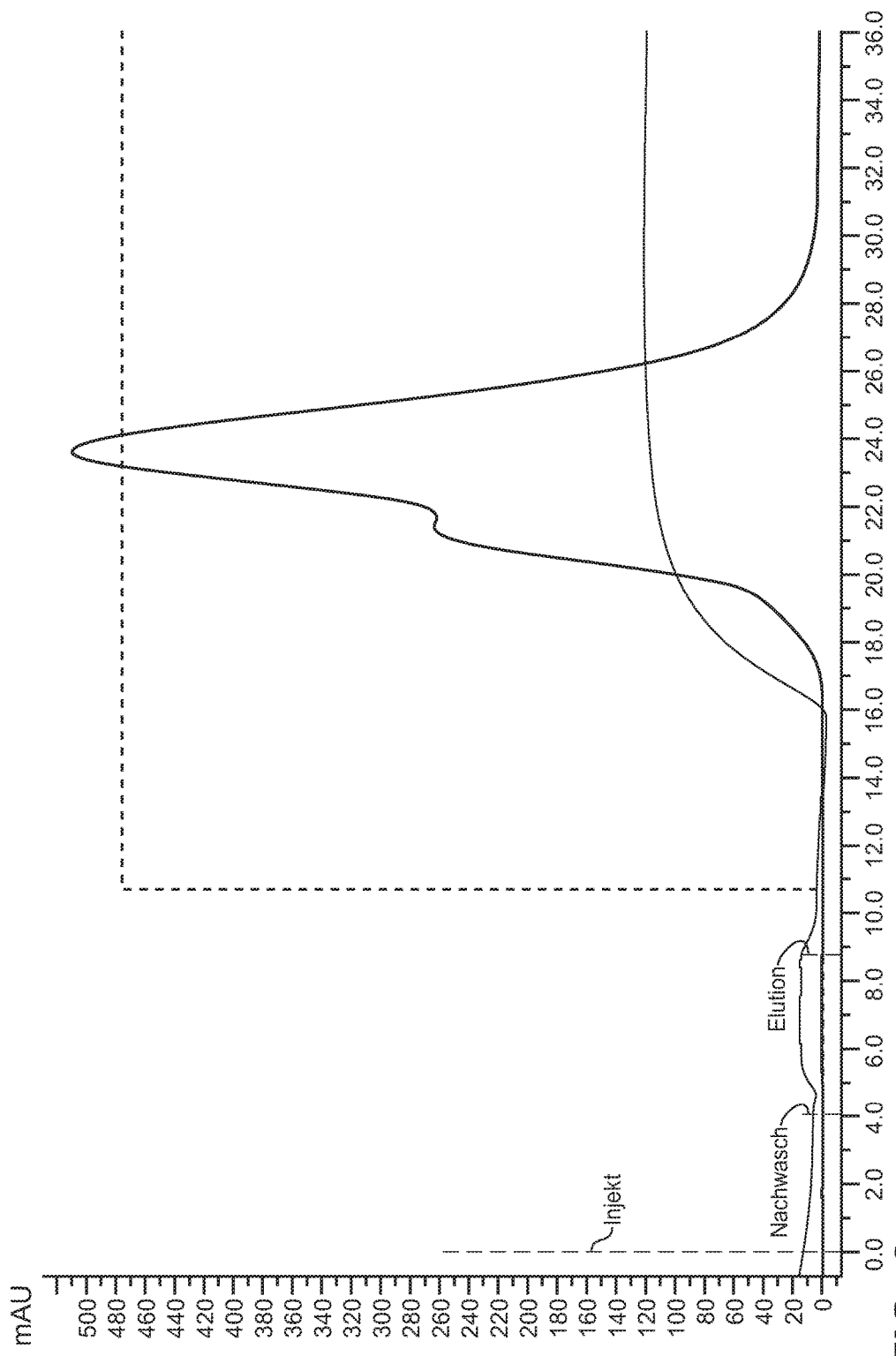
FIG. 2 Elution chromatogram of a column chromatographic separation using a step gradient of 24 vol % elution buffer is shown (wash buffer comprises 20 mM sodium citrate, elution buffer comprises 20 mM sodium citrate and 100 mM sodium chloride).

Chromatography with Step Gradient Elution to 24 Vol % Elution Buffer on SP-Sepharose Chromatographic Conditions:
Resin: Highscreen SP-Sepharose
Flow rate: 1.2 ml/min
Equilibration: 20 mM sodium citrate, adjusted to pH 6.2
Loading: 1 g protein/1 chromatography material
Wash: 20 mM sodium citrate, adjusted to pH 6.2
Elution: 20 mM sodium citrate, adjusted to pH 6.2 and supplemented with 100 mM sodium chloride
Elution Method:
   single step gradient
   step to 24% elution buffer and elution over 20 column volumes The elution chromatogram is shown in FIG. 2. It can be seen that the antibody isoforms can be recovered in a semi-detached peak.

Example 3

Figure 3:
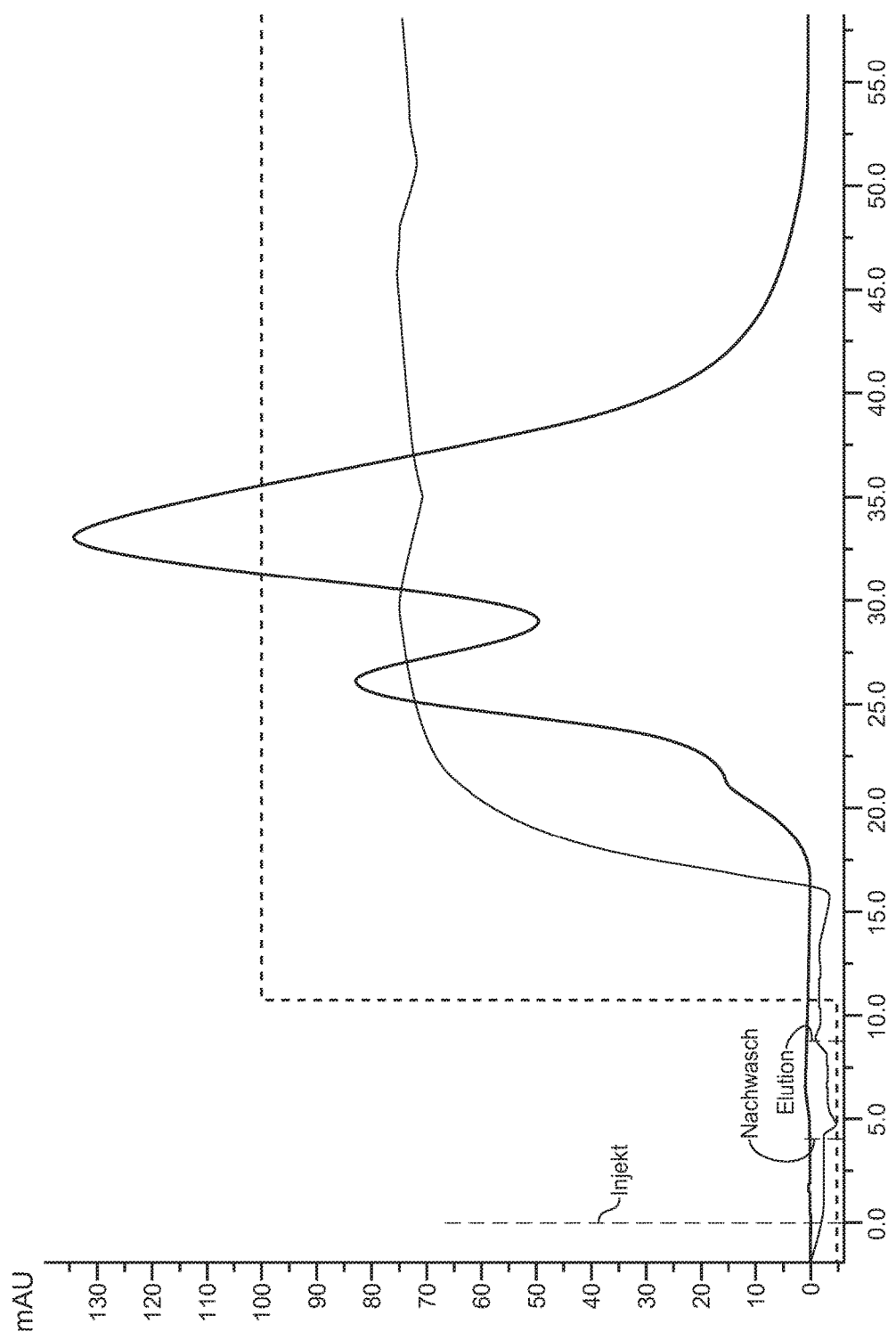
FIG. 3 Elution chromatogram of a column chromatographic separation using a step gradient of 15 vol % elution buffer is shown (wash buffer comprises 20 mM sodium citrate, elution buffer comprises 20 mM sodium citrate and 80 mM sodium chloride).

Chromatography with Step Gradient Elution to 15 Vol % Elution Buffer on SP-Sepharose Chromatographic Conditions:
Resin: Highscreen SP-Sepharose
Flow rate: 1.2 ml/min
Equilibration: 20 mM sodium citrate, adjusted to pH 6.2
Loading: 1 g protein/1 chromatography material
Wash: 20 mM sodium citrate, adjusted to pH 6.2
Elution: 20 mM sodium citrate, adjusted to pH 6.2 and supplemented with 80 mM sodium chloride
Elution Method:
   single step gradient
   step to 15% elution buffer and elution over 20 column volumes The elution chromatogram is shown in FIG. 3. It can be seen that the antibody isoforms can be recovered in two semi-detached peak, wherein the first peak shows a pre-peak.

Example 4

Figure 4:
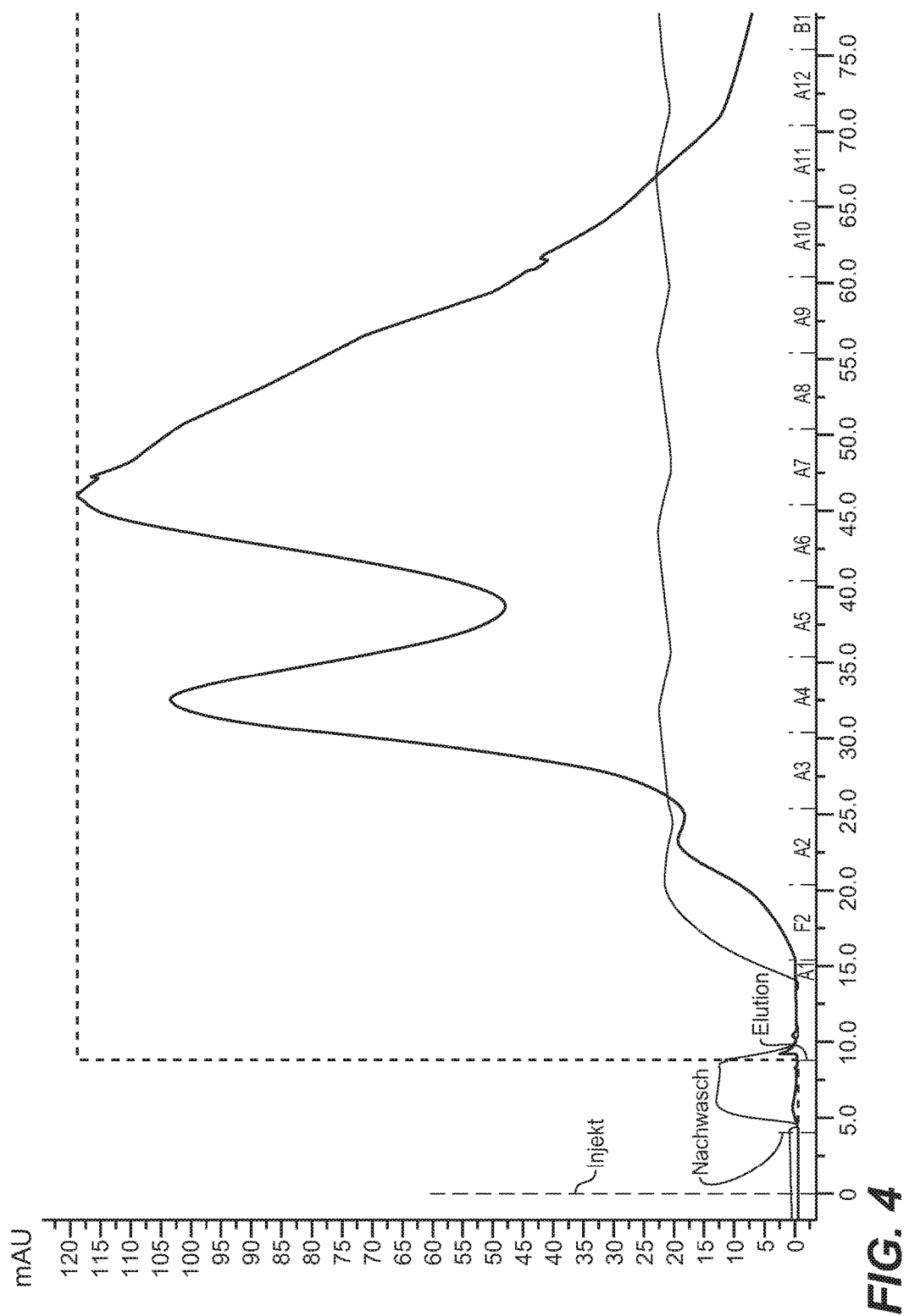
FIG. 4 Elution chromatogram of a column chromatographic separation using a step gradient of 100 vol % elution buffer is shown (wash buffer comprises 20 mM sodium citrate, elution buffer comprises 20 mM sodium citrate and 5 mM sodium chloride).

Chromatography with Step Gradient Elution to 100 Vol % Elution Buffer on SP-Sepharose Chromatographic Conditions:
Resin: Highscreen SP-Sepharose
Flow rate: 1.2 ml/min
Equilibration: 20 mM sodium citrate, adjusted to pH 6.2
Loading: 1 g protein/1 chromatography material
Wash: 20 mM sodium citrate, adjusted to pH 6.2
Elution: 20 mM sodium citrate, adjusted to pH 6.2 and supplemented with 5 mM sodium chloride
Elution Method:
  single step
  single step to 100% elution buffer and elution over 20 column volumes The elution chromatogram is shown in FIG. 4. It can be seen that the antibody isoforms can be recovered in three semi-detached peaks.

Example 5

Chromatography with pH Gradient Elution to 100 Vol % Elution Buffer on MonoS Strong Cation Exchange Resin Chromatographic Conditions:
Resin: MonoS
Equilibration: 20 mM sodium citrate, adjusted to pH 5.2
Wash: 20 mM sodium citrate, adjusted to pH 5.2
Elution: 50 mM sodium phosphate, adjusted to pH 7.5
Elution Method:
  gradient elution
  from 0% to 100% elution buffer.

The isoforms can be obtained as three semi-detached peaks.

Example 6

Comparative Example

Chromatographic Separation of a Monoclonal Anti-HER-2 Antibody (WO 99/57134) with a Strong Cation Exchange Resin (SP-Sepharose)

Figure 5:
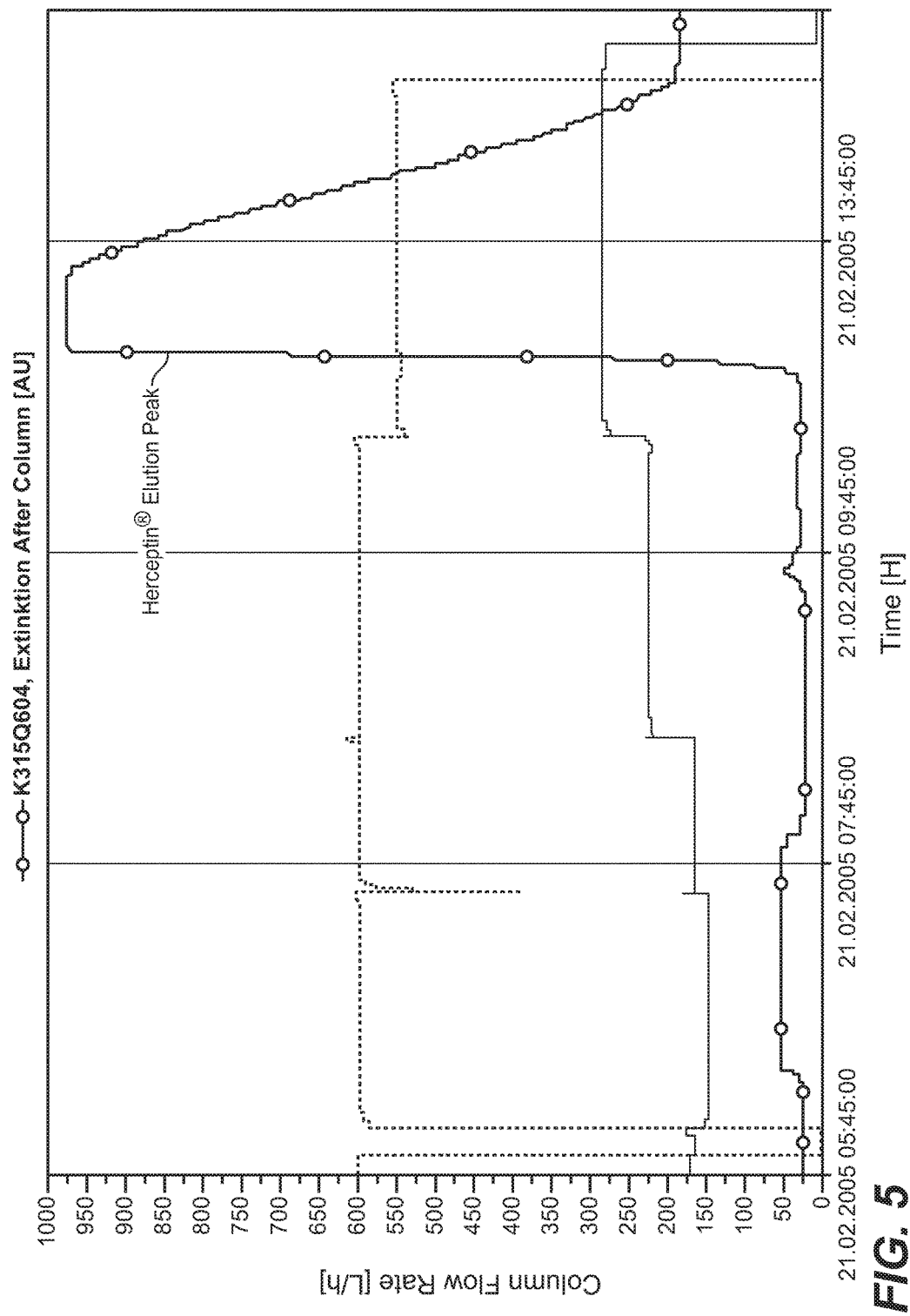
FIG. 5 Single step elution of anti-HER-2 antibody from strong cation exchange resin SP-Sepharose; monomeric and aggregated forms of the antibody are not separated and elute as one peak.

The purification of a monoclonal anti-HER2 antibody (Herceptin®) with a cation exchange chromatography on SP-Sepharose, a strong cation exchange resin, was carried out. Under standard conditions, i.e. step elution with e.g. sodium chloride, a separation of monomeric and aggregated forms of the antibody is not effected (FIG. 5).
Chromatographic Conditions:
Resin: SP-Sepharose
Flow rate: 160 cm/h
Equilibration: 25 mM 2-morpholinoethanesulfonic acid, 50 mM sodium chloride, adjusted to pH 5.6
Loading: max. 20 g protein/L gel matrix
Wash: 25 mM 2-morpholinoethanesulfonic acid, 50 mM sodium chloride, adjusted to pH 5.6
Elution: 25 mM 2-morpholinoethanesulfonic acid, 95 mM sodium chloride, adjusted to pH 5.6

The monoclonal anti-HER-2 antibody was purified in a first step with a protein A affinity chromatography. Elution from the protein A column is carried out under acidic conditions (10 mM sodium citrate buffer, pH value of 3.0±0.5). Before the filtration step the pH value of the fraction containing the antibody is adjusted with a concentrated tris-hydroxymethyl-amino-methane (TRIS) buffer to pH 5.6. The protein A eluate is a solution with a protein concentration between 5 mg/ml and 15 mg/ml and is buffered with sodium citrate.

The conditioned protein A eluate was applied to a chromatography column containing a strong cation exchange resin (SP-Sepharose). After the loading step at a flow rate of 160 cm/h the column was washed with equilibration buffer (10 column volumes). The bound immunoglobulins were eluted with a single step elution method, whereby the pH value was kept constant and the conductivity was varied by the (stepwise) increase of the sodium chloride concentration. The elution chromatogram is displayed in FIG. 5.

No separation of monomeric and aggregated forms of the antibody was achieved.

Example 7

Chromatography with Gradient Elution to 60 Vol % Elution Buffer on Source™ 15S

Figure 6:
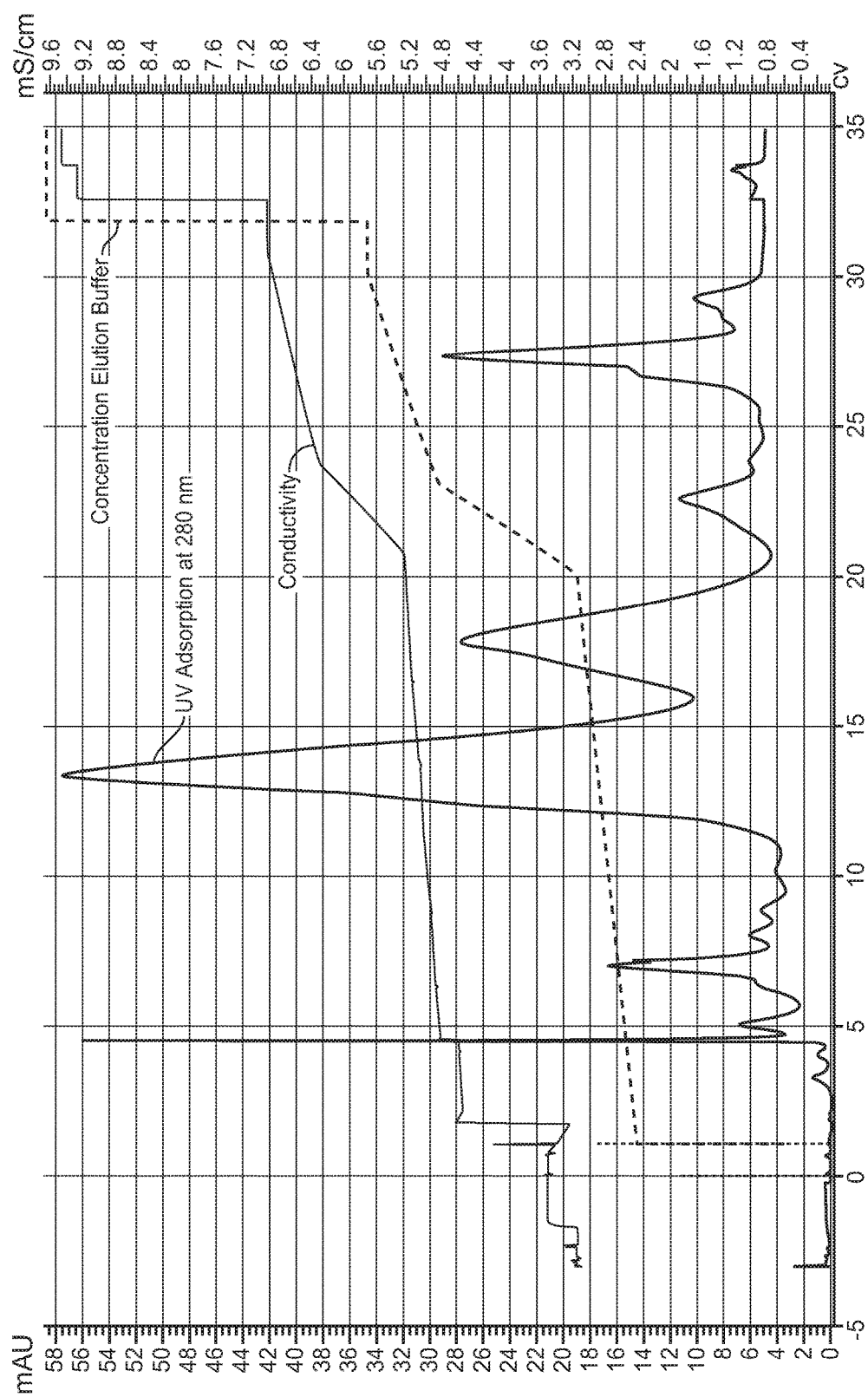
FIG. 6 Elution chromatogram of a column chromatographic separation using a linear gradient to 60 vol % elution buffer is shown (wash buffer comprises 25 mM TRIS and 10 mM sodium chloride, elution buffer comprises 25 TRIS and 70 mM sodium chloride).

Chromatographic Conditions:
Resin: Source™ 15 S
Column volume: 1.141
Flow rate: 100 cm/h
Equilibration: 25 mM TRIS, 10 mM sodium chloride, adjusted to pH 7.4
Loading: 0.88 g protein/1 chromatography material
Wash: 25 mM TRIS, 10 mM sodium chloride, adjusted to pH 7.4
Elution: 25 mM TRIS, 70 mM sodium chloride, adjusted to pH 7.4
Elution Method:
  gradient
  to 33 vol % elution buffer in 19 column volumes
  to 50 vol % elution buffer in 3 column volumes
  to 60 vol % elution buffer in 7 column volumes The elution chromatogram is shown in FIG. 6. It can be seen that the antibody isoforms can be recovered in defined peak.

The invention claimed is:
1. A method for producing an antibody preparation comprising the following steps:
  a) applying a buffered solution comprising different isoforms of an antibody to a cation exchange chromatography material,
  b) applying a first solution with a first conductivity to the cation exchange chromatography material, whereby the antibody isoforms remain adsorbed to the cation exchange chromatography material,
  c) applying a second solution with a second conductivity to the cation exchange chromatography material and thereby obtaining the antibody preparation,
  wherein the conductivity of the second solution exceeds the conductivity of the first solution by not more than 10%,
  wherein the cation exchange chromatography material has a swellable matrix,
  wherein the first solution is changed to a second solution in a single step, wherein the conductivity of the first solution I from 4 mS/cm to 5 mS/cm, and wherein the buffered solution is a citrate buffered solution.

2. A method for producing an antibody preparation comprising the following steps:
   a) cultivating a mammalian cell comprising a nucleic acid encoding the antibody and recovering the antibody from the cell or the cultivation medium,
   b) purifying the antibody by at least one column chromatographic step, wherein the at least one chromatographic step comprises the following steps:
      i) applying a buffered solution comprising different isoforms of the antibody to a cation exchange chromatography material,
      ii) applying a first solution with a first conductivity to the cation exchange chromatography material, whereby the antibody isoforms remain bound to the cation exchange chromatography material, and
      iii) applying a second solution with a second conductivity to the cation exchange chromatography material and thereby producing the antibody preparation,
   wherein the conductivity of the second solution exceeds the conductivity of the first solution by not more than 10%,
   wherein the cation exchange chromatography material has a swellable matrix,
   wherein the first solution is changed to the second solution in a single step,
   wherein the conductivity of the first solution is from 4 mS/cm to 5 mS/cm, and
   wherein the buffered solution is a citrate buffered solution.

3. The method according to claim 1 or 2, characterized in that the swellable matrix is agarose.

4. The method according to claim 1 or 2, characterized in that the cation exchange chromatography material is a strong cation exchange chromatography material.

5. The method according to claim 4, characterized in that the strong cation exchange chromatography material is a sulfopropyl-cation exchange chromatography material.

6. The method according to claim 1 or 2, characterized in that the single step is a change from 100 vol % of the first solution to 100 vol % of the second solution.

7. The method according to claim 1 or 2, characterized in that the first solution comprises 20 mM sodium citrate and 10 mM sodium chloride or 25 mM TRIS and 10 mM sodium chloride.

8. The method according to claim 1 or 2, characterized in that the second solution comprises 20 mM sodium citrate and 5 mM sodium chloride or 25 mM TRIS and 70 mM sodium chloride.

9. The method according to claim 1 or 2, characterized in that the antibody is an anti-HER2 antibody.

10. The method according to claim 9, characterized in that the anti-HER2 antibody is the anti-HER2 antibody trastuzumab or the anti-HER2 antibody Pertuzumab.

* * * * *